United States Patent [19]
Joensen

[11] Patent Number: 5,840,969
[45] Date of Patent: Nov. 24, 1998

[54] PROCESS FOR THE PREPARATION OF ACETIC ACID FROM A SYNTHESIS GAS OF HYDROGEN AND CARBON MONOXIDE

[75] Inventor: Finn Joensen, Hørsholm, Denmark

[73] Assignee: Haldor Topsoe A/S, Lyngby, Denmark

[21] Appl. No.: 979,527

[22] Filed: Nov. 26, 1997

[30] Foreign Application Priority Data

Nov. 29, 1996 [DK] Denmark .................................. 1361/96

[51] Int. Cl.⁶ .................................................. C07C 51/12
[52] U.S. Cl. ............................................................ 562/519
[58] Field of Search .............................................. 562/519

[56] References Cited

U.S. PATENT DOCUMENTS

| | | | |
|---|---|---|---|
| 3,769,329 | 10/1973 | Paulik et al. ............................ | 260/488 |
| 4,255,591 | 3/1981 | Makin et al. ............................ | 562/517 |
| 5,189,203 | 2/1993 | Hansen et al. ........................... | 560/232 |
| 5,286,900 | 2/1994 | Hansen et al. ........................... | 560/232 |
| 5,371,286 | 12/1994 | Blay et al. ............................... | 562/519 |

FOREIGN PATENT DOCUMENTS

| | | | |
|---|---|---|---|
| 0250189 | 12/1987 | European Pat. Off. ......... | C07C 53/08 |
| 0801050 | 10/1997 | European Pat. Off. ......... | C07C 53/08 |
| 2301101 | 11/1996 | United Kingdom ............ | C07C 51/12 |

*Primary Examiner*—Gary Geist
*Assistant Examiner*—Rosalynd Keys
*Attorney, Agent, or Firm*—Ostrolenk, Faber, Gerb & Soffen, LLP

[57] ABSTRACT

A process for the preparation of acetic acid product comprising, in a first catalytic step, conversion of a hydrogen and carbon monoxide containing synthesis gas to obtain a liquid process stream comprising methanol and, in a second catalytic step, carbonylation of the process stream with carbon monoxide to a product stream being rich in the acetic acid product in presence of catalytic effective amounts of a metal compound selected from Group VIII of the Periodic Table promoted with a halide compound, the improvement comprising the further steps of:

(i) withdrawing from the carbonylation step a vent gas stream comprising carbon monoxide and residual amounts of acetic acid and halide compound;

(ii) separating the vent gas stream into a liquid fraction containing a part of the residual amounts of acetic acid and part of the halide compound and a gaseous fraction with the carbon monoxide and remaining amounts of acetic acid and halide compound;

(iii) recycling the liquid fraction to the carbonylation step;

(iv) subjecting the gaseous fraction to liquid absorption to remove the acetic acid and halide compound in the gaseous fraction to obtain a carbon monoxide rich recycle stream; and (v) introducing the carbon monoxide rich recycle stream into the synthesis gas conversion step.

6 Claims, 3 Drawing Sheets

PROCESS FOR THE PREPARATION OF ACETIC ACID FROM A SYNTHESIS GAS OF HYDROGEN AND CARBON MONOXIDE

FIELD OF THE INVENTION

The present invention relates to preparation of acetic acid from a synthesis gas of hydrogen and carbon oxides. More particular, the invention comprises catalytic steps of converting hydrogen and carbon monoxide in the gas to a process stream containing methanol or methanol/dimethyl ether (DME) and carbonylating methanol or methanol/DME formed in the process stream into acetic acid.

BACKGROUND OF THE INVENTION

The conventional process for the manufacture of acetic acid presently widely used in the industry includes catalytic carbonylation of methanol as disclosed by e.g. U.S. Pat. No. 3,769,329 and EP Pat. No. 250,189.

Catalysts usually employed in the carbonylation reaction comprise a rhodium compound promoted with methyl iodide.

The conventional acetic acid process, however, requires supply of methanol reactant from external sources.

A possible route to eliminate the need for external supply of methanol may be to integrate synthesis of methanol into the acetic acid process by producing methanol and carbon monoxide in parallel.

This approach is, in particular, convenient when both reactants are prepared from synthesis gas obtained at high efficiency through steam reforming of natural gas.

The major drawback in parallel production of methanol and carbon monoxide is the reaction pressure required in the methanol synthesis, which in order to achieve acceptable conversion rates must be significantly higher than the pressure typically used in the subsequent acetic acid synthesis step.

The above problem with different synthesis pressure in the methanol and subsequent acetic acid synthesis is overcome by introduction of a combined methanol/dimethyl ether synthesis in the first reaction step of the acetic acid preparation process, as disclosed in U.S. Pat. Nos. 5,189,203 and 5,286,900.

Simultaneous preparation of methanol and DME from hydrogen and carbon oxides containing synthesis gas is catalyzed by a number of catalysts such as the known methanol catalyst including mixed oxides of Cu/Zn/Cr or Cu/Zn/Al and methanol dehydration catalysts such as alumina, silica-alumina, zeolitic materials, silica alumino phosphates and heteropoly acids of Mo and W being applied as physical mixture or prepared by impregnation on carrier materials, co-pelletization or co-precipitation.

In the process disclosed in the later US patents, combined methanol and DME synthesis are followed by carbonylation of methanol and DME to acetic acid products. An advantageous feature of these processes is that the simultaneous conversion of synthesis gas to methanol and DME may be performed efficiently at high conversion at a pressure substantially corresponding to the synthesis pressure in the subsequent acetic acid reaction step.

The above process requires excess of carbon monoxide in the feed gas for the methanol/DME synthesis in order to leave sufficient concentration of the carbon monoxide in the effluent from the methanol/DME synthesis for the carbonylation reaction in the subsequent acetic acid synthesis. As a consequence of the CO concentration being in excess of the stoichiometric requirement in the methanol/DME synthesis, significant amounts of carbon dioxide are formed by the following reaction:

$$5CO+3H_2 \rightarrow CH_3OCH_3+2CO+CO_2 \quad (1)$$

High carbon dioxide concentration in the effluent from the methanol/DME synthesis represents the major draw-back of this process. Carbon dioxide acts essentially as an inert gas in the carbonylation reaction and, therefore, necessitates significantly higher synthesis pressure in the acetic acid reaction step in order to maintain a sufficient pressure of carbon monoxide.

Acetic acid preparation from a hydrogen and carbon monoxide containing synthesis gas including synthesis of methanol and DME at a high hydrogen/carbon monoxide ratio in the synthesis gas in a first catalytic reaction stage and subsequent carbonylation of the effluent from the first reaction stage to acetic acid product with added carbon monoxide are described in Danish Patent Application No. 96/0407.

As a major improvement of the latter process, excess of carbon monoxide is avoided in the methanol/DME synthesis by separating a part of the monoxide from the synthesis gas prior to the methanol/DME synthesis and introducing separated amounts of the carbon monoxide directly into the carbonylation stage.

SUMMARY OF THE INVENTION

It has now been found that the known processes for the preparation of acetic acid may still be improved and consumption of synthesis gas in the process advantageously be reduced, when recycling unconverted amounts of carbon monoxide from the carbonylation reaction in the final acetic acid preparation step back to the synthesis gas conversion step.

Pursuant to this finding, this invention is a process for the preparation of acetic acid product through:

conversion of a hydrogen and carbon monoxide containing synthesis gas to obtain a liquid process stream comprising methanol and, subsequently, in carbonylation of the process stream with carbon monoxide to a product stream being rich in the acetic acid product in presence of catalytic effective amounts of a metal compound selected from Group VIII of the Periodic Table promoted with a halide compound, the improvement comprising further steps of:

(i) withdrawing from the carbonylation step a vent gas stream comprising carbon monoxide and residual amounts of acetic acid and halide compound;

(ii) separating the vent gas stream into a liquid fraction containing a part of the residual amounts of acetic acid and part of the halide compound and a gaseous fraction with the carbon monoxide and remaining amounts of acetic acid and halide compound;

(iii) recycling the liquid fraction to the carbonylation step;

(iv) subjecting the gaseous fraction to liquid absorption to remove the acetic acid and halide compound in the gaseous fraction to obtain a carbon monoxide rich recycle stream; and (v) introducing the carbon monoxide rich recycle stream into the synthesis gas conversion step.

In a preferred embodiment of the invention, the process stream to be carbonylated contains a mixture of methanol and dimethyl ether.

DETAILED DESCRIPTION OF THE INVENTION

Figure 1:
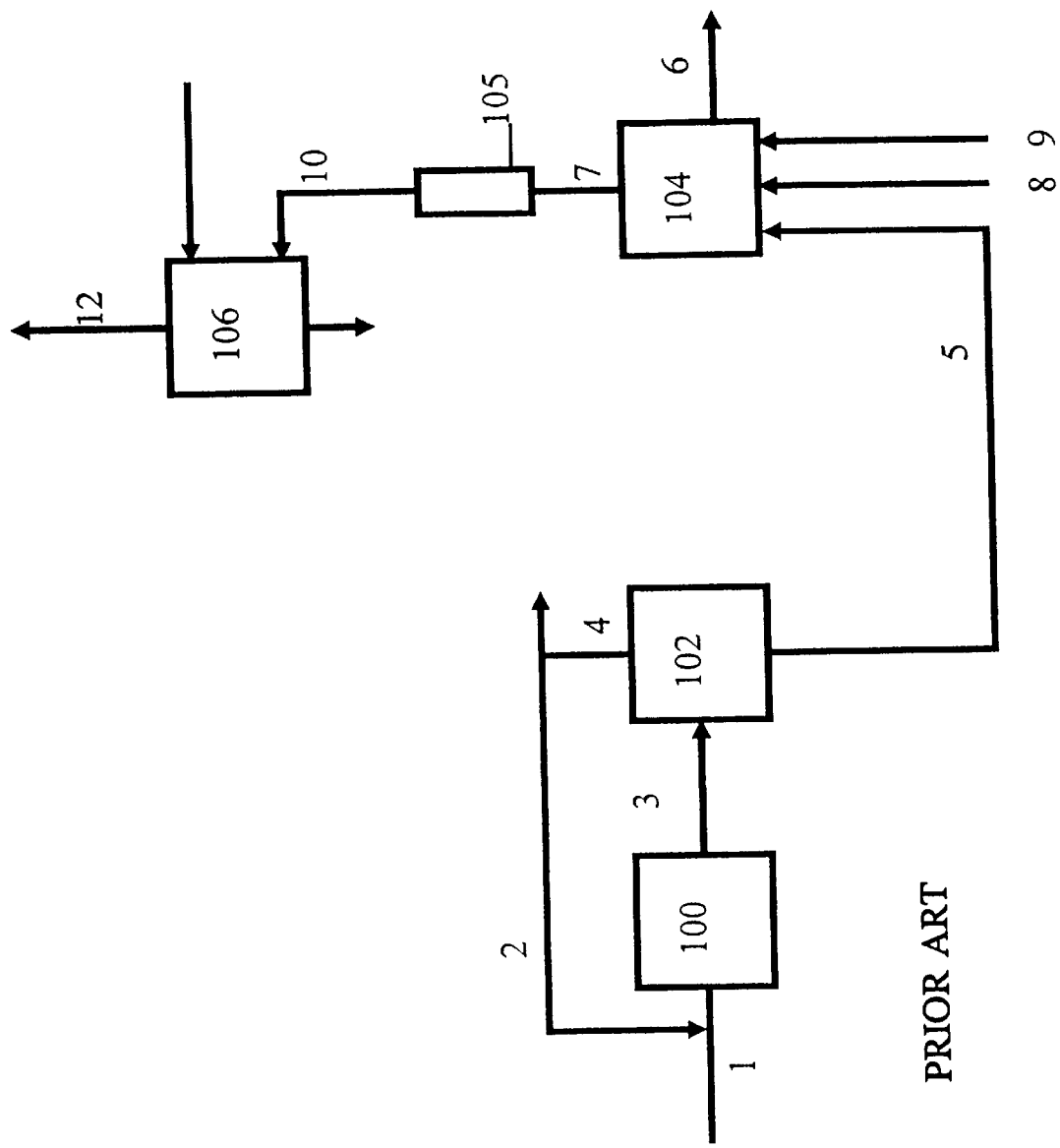
FIG. 1 shows a prior art process for making acetic acid.
Figure 2:
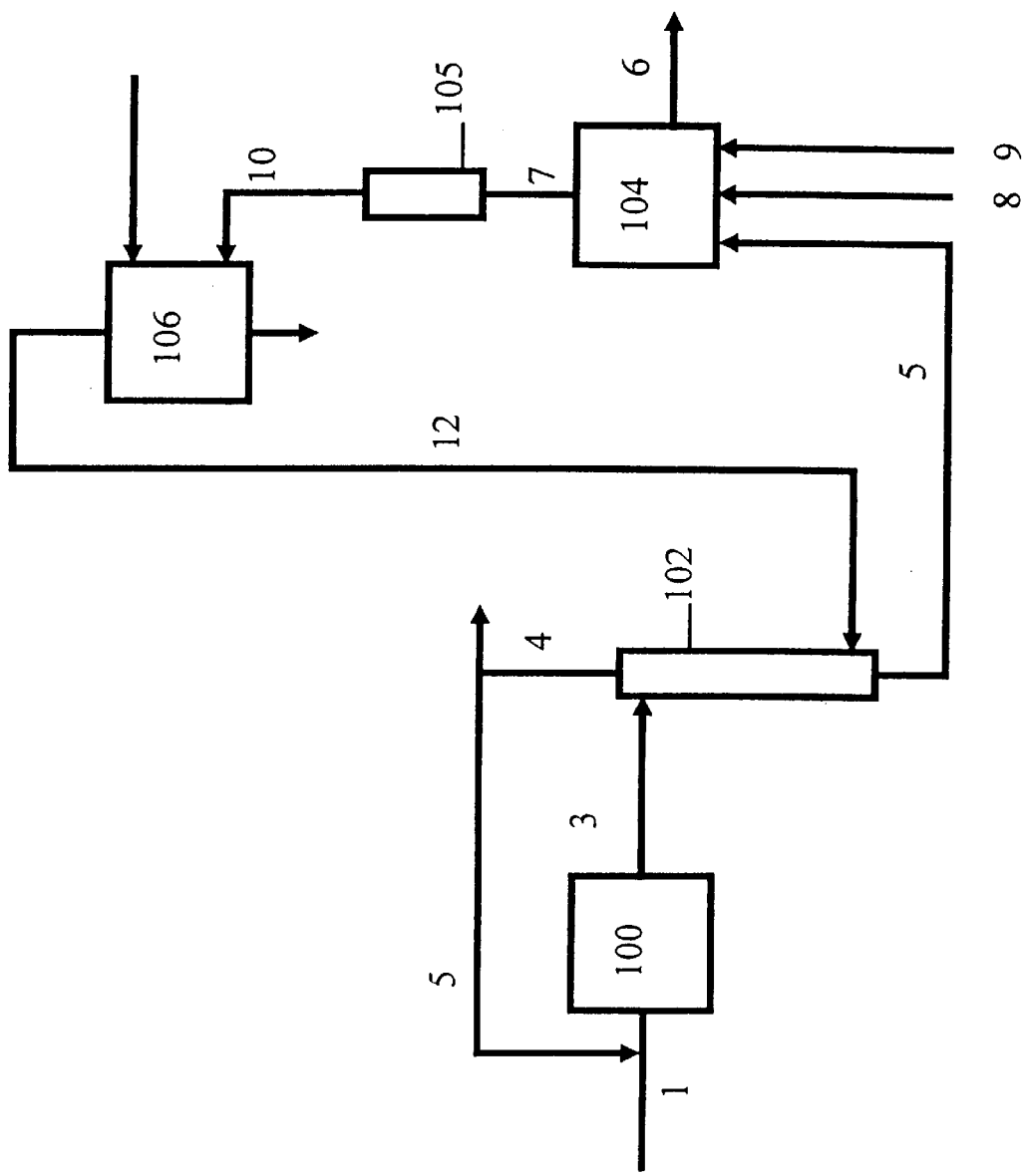
FIG. 2 shows the process for making acetic acid of the present invention in which carbon monoxide utilization is substantially increased by recycling the vent gas stream.

As initially mentioned, the combined synthesis of methanol and DME are performed in presence of a catalytic system catalyzing the formation of methanol and dehydration of methanol to DME by the reactions:

$$CO + 2H_2 \leftrightarrow CH_3OH \qquad (2)$$

$$2CH_3OH \leftrightarrow CH_3OCH_3 + H_2O \qquad (3)$$

Those catalysts include the aforementioned catalysts and, in particular, catalysts having a composition of about 60 atom % Cu, 25 atom % Zn and 15 atom % Al being highly active in the methanol forming reaction (2) and alumina or alumina silicates for the DME reaction (3).

The catalysts in the first process step may be arranged in a fixed bed of an intimately admixture or as a layered bed with alternating methanol synthesis and methanol dehydration catalyst particles. Physical mixtures of the catalyst result, however, in lower selectivity and it is often preferred to employ a fixed bed of a catalyst composition with combined methanol, and methanol dehydration activity. Such catalyst composition may be prepared by impregnation, copelletization or coprecipitation of the catalytic active materials in accordance with the known methods in the manufacture of catalysts.

Through contact with the above catalyst compositions hydrogen and carbon monoxide in the feed gas are by the above reactions (2) and (3) converted to methanol, DME and water. Part of the produced water is shifted to carbon dioxide and hydrogen by the water gas shift reaction:

$$H_2O + CO \leftrightarrow CO_2 + H_2 \qquad (4),$$

proceeding simultaneously with reactions (2) and (3).

As discussed before, the acetic acid processes disclosed in U.S. Pat. Nos. 5,189,203 and 5,286,900 utilizing combined methanol/DME synthesis in a first reaction step require in the feed gas excess of carbon monoxide in relation to the stoichiometric requirement in the methanol and DME forming reaction (2) in order to leave in the effluent from the methanol/DME reactions the necessary amount of carbon monoxide for the carbonylation of the reaction products in the subsequent acetic acid preparation step.

In contrast to the known processes, the process of this invention may be operated advantageously with a high hydrogen/carbon monoxide ratio in the feed gas to the methanol/DME reaction. The hydrogen/carbon monoxide ratio required in the feed gas is typically between 2:1 and 3:1, as supplied by unadjusted synthesis gas from conventional steam reforming of a hydrocarbon feedstock. Thereby, substantially all amounts of carbon monoxide in the feed gas are converted to DME and methanol and formation of inert carbon dioxide by-product are considerably reduced. Conversion levels similar to those of the conventional methanol synthesis are achieved at a synthesis pressure of 25–50 bar, which correspond to the required pressure in the subsequent acetic acid reaction step.

Produced methanol, DME and water are recovered in a liquid process phase from the effluent of the above reaction step by cooling the effluent and recycling of the gaseous phase containing unconverted feed gas and carbon dioxide. A minor part of the gaseous phase is purged to avoid build-up of inerts, such as nitrogen, argon and methane, in the synthesis loop. Due to the relatively high vapour pressure of DME, the purge gas contains further a part of produced DME. Therefore, it is preferred to subject the purge gas from the above effluent to a purge wash with a suitable liquid washing agent, preferably methanol or acetic acid. DME recovered from the purge gas is then combined with the liquid process phase.

In the final reaction step of the invention, catalytic carbonylation of DME and methanol to acetic acid are carried out with carbon monoxide being supplied to the reaction as a separate stream.

Carbon monoxide is introduced into the carbonylation step in an amount corresponding at least to the stoichiometric amount in the carbonylation reaction:

$$CH_3OH + CO \rightarrow CH_3COOH \qquad (5)$$

$$CH_3OCH_3 + 2CO + H_2O \; 2CH_3COOH \qquad (6)$$

To provide sufficient amount of carbon monoxide reactant, the monoxide will be added in an amount resulting in a mole ratio of carbon monoxide and methanol plus DME, i.e.

$$CO/(CH_3OH + 2CH_3OCH_3),$$

in the carbonylation reaction in the range of between 1 to 1.5.

To provide a sufficient amount of water to satisfy a stoichiometric ratio between DME and water in eq. (6) of about one, additional water is added to the carbonylation step.

A number of catalyst systems being active in the above carbonylation reactions are known in the art. Catalysts usually employed are based on a combination of Group VIII transition metal compounds and a halogen compound promoter. In addition thereto, a number of secondary promoters have been disclosed in the art, comprising metal salts and organic compounds.

Preferred catalysts for use in the invention include compounds of group VIII metals of the Periodic System promoted with iodine or bromine compounds, e.g. methyl iodide.

The carbonylation reactions may be carried out within a wide range of temperatures from about 100° C. to 400° C., though temperatures between 150° C. and 250° C. are sufficient to obtain reasonable reaction conditions.

Preferably, the reaction is performed in liquid phase at elevated pressure by establishing a partial pressure of the carbon monoxide in the gas phase over the liquid reaction phase in the reactor being sufficiently high to provide sufficient concentration of dissolved carbon monoxide in the liquid phase for the carbonylation reactions proceeding in this phase. Typically, the pressure will be in the range of 25–50 bar depending on the reaction temperature and catalyst concentration. Carbon monoxide is usually introduced continuously at the bottom of the reactor and bubbled through the liquid process phase in a predetermined amount to reach the desired yield of acetic acid product in the carbonylation reactions as mentioned above.

Carbon monoxide may be supplied from a substream of the carbon monoxide containing synthesis gas by conventional separation methods, such as cryogenic separation or separation of the monoxide in a membrane unit, wherein hydrogen in the gas with high selectivity permeates through a hollow fibre membrane, and carbon monoxide is recovered in the residue stream of the membrane unit.

In the carbonylation, reaction step part of carbon monoxide is converted into carbon dioxide through the water gas shift reaction:

$$CO + H_2O \rightarrow CO_2 + H_2$$

In addition, the carbon monoxide reactant gas usually contains small amounts of inerts such as methane, nitrogen and argon. In order to avoid build-up of $CO_2$ and hydrogen and inerts in the carbonylation reactor, which reduces the CO partial pressure, the overhead gas phase must be vented by passing an excess amount of carbon monoxide through the reaction solution.

By continuously withdrawing vent gas being rich in carbon monoxide, the concentration of hydrogen, carbon dioxide and inerts in the gas phase are maintained at an acceptable low level.

In addition to carbon monoxide, hydrogen, carbon dioxide and inerts the vent gas contains methyl iodide, water and acetic acid vapours. In order to recover these values the gas stream is cooled whereby part of the condensible fraction is recovered and recycled to the reactor. However, after separation of the condensed phase the gaseous phase still contains considerable amounts of methyl iodide. To recover methyl iodide, the gas is passed to a methyl iodide absorber where methyl iodide is absorbed in a liquid absorption medium, preferably acetic acid or aqueous acetic acid and subsequently stripped off in a methyl iodide stripper column and returned to the carbonylation step.

The purge gas from the absorber unit consists of carbon monoxide, hydrogen, carbon dioxide and inerts together with traces of methyl iodide. The gas further contains minor amounts of the acetic acid absorption agent. Due to the content of hydrogen, carbon dioxide and inerts, the purge gas cannot be recycled to the carbonylation step.

By the process of this invention, the vent gas is advantageously utilized in the synthesis gas conversion reactions allowing for the efficient conversion of carbon monoxide, hydrogen and carbon dioxide into methanol or methanol/dimethyl ether.

The vent gas to be recycled inevitably contains small amounts of the acetic acid washing agent as well as traces of methyl iodide. Both substances may act as inhibitors or even poison to the catalysts applied in the synthesis gas conversion step. It is, therefore, necessary that acetic acid and methyl iodide traces are efficiently removed before introducing the vent gas stream into the conversion step.

This is achieved by introducing the vent gas into the liquid product phase obtained in the synthesis gas conversion step consisting of methanol, dimethyl ether and water and using the liquid phase as a second washing agent for the removal of acetic acid and traces of methyl iodide. Preferably, the vent gas is introduced countercurrently to the liquid product flow in liquid product separator. The bottom of separator is, therefore, preferably equipped with trays or packing material to improve the absorption process.

In another embodiment of the invention the vent gas is introduced directly to the liquid product phase obtained in the synthesis gas conversion step without being passed through a methyl iodide absorber.

The essential steps of the invention are further illustrated in the following examples.

Example 1

(Comparison Example)

This Example demonstrates that significant amounts of carbon monoxide are not utilized when the carbonylation step is carried out by the known processes. Reference is made to FIG. 1 in the Drawings and Table 1 summarizing the results of relevant process streams.

30223 $Nm^3/h$ of a synthesis gas feed stream 1 are mixed with process recycle gas stream 2 and converted in a first catalytic step in reactor 100 at a pressure of 39 bar and a temperature of between 240° C. and 290° C. to obtain a reactor effluent stream 3 containing methanol, dimethyl ether and water.

The reactor effluent stream 3 is cooled to produce a liquid phase containing methanol, dimethyl ether and water and a gaseous phase containing hydrogen, carbon monoxide and carbon dioxide and inerts such as methane.

The cooled reactor effluent stream is passed to separator 102 from which is withdrawn 9950 kg/h of a liquid process stream 5 containing liquid products of stream 3 and a gaseous stream 4 containing unconverted synthesis gas and inerts. Part of the gaseous stream 4 is purged to avoid build-up of inerts in the synthesis loop and the remainder is recycled as stream 2.

Stream 5 is passed to acetic acid reactor 104 in which methanol, dimethyl ether and water are reacted in a second catalytic step with 8760 $Nm^3/h$ of 93 mole % carbon monoxide, the remainder being hydrogen and methane, added as stream 8 to form acetic acid at a pressure of 35 bar and 185° C. by employing a catalyst system comprising a rhodium catalyst and a methyl iodide promoter. In reactor 104 part of the carbon monoxide reacts with water to produce carbon dioxide and hydrogen by the water gas shift reaction. A stream 9 of 300 kg/h of water is added to reactor 104 in order to maintain a finite water concentration.

From reactor 104 is obtained a liquid stream 6 containing the acetic acid product corresponding to 18740 kg/h of acetic acid and a gaseous stream 7 containing acetic acid, water, methyl iodide, hydrogen, carbon dioxide and unconverted carbon monoxide and inerts such as methane.

The gaseous stream 7 is passed through reflux condenser 105 to recover part of condensibles comprising acetic acid, water and methyl iodide which are recycled to the reactor 104 and the resulting gaseous stream 10 is passed to absorber 106, in which essentially all methyl iodide is recovered by absorption in liquid acetic acid.

From absorber 106 is obtained 1520 $Nm^3/h$ of a vent gas stream 12 containing unconverted carbon monoxide together with hydrogen and carbon dioxide and inerts and additional small amounts of acetic acid and traces of methyl iodide.

In Example 1, 88.4% of the total carbon monoxide contained in the feed streams 1 plus 9 is converted into acetic acid.

Example 2

This Example demonstrates how the overall carbon monoxide utilization is substantially increased by recycling the vent gas stream 12 of Example 1 to the first catalytic step. Reference is made to Drawing and Table 2.

27523 $Nm^3/h$ of a synthesis gas stream 1 are converted in the way described in Example 1 to obtain a reactor effluent stream 3 containing methanol, dimethyl ether and water.

The reactor effluent stream 3 is cooled to produce a liquid phase containing methanol, dimethyl ether and water and a gaseous phase containing hydrogen, carbon monoxide and carbon dioxide and inerts such as methane.

The cooled reactor effluent stream is passed to absorber 102 and contacted countercurrently with 1520 $Nm^3/h$ of an acetic acid reactor vent gas stream 12 containing as the main components carbon monoxide, hydrogen and methane and minor amounts of acetic acid and traces of methyl iodide.

From the absorber 102 is withdrawn 9960 kg/h of a liquid process stream 5 containing liquid products of stream 3 and acetic acid and traces of methyl iodide contained in stream 12 and a gaseous stream 4 containing unconverted synthesis gas and inerts of the first catalytic step and carbon monoxide, hydrogen, carbon dioxide and inerts of stream 12. Part of the combined gaseous stream 4 is purged to avoid build-up of inerts in the synthesis loop and the remainder is recycled as stream 2.

Stream 5 is passed to acetic acid reactor 104 in which methanol, dimethyl ether and water are reacted in a second catalytic step with 8760 Nm³/h of 93 mole % carbon monoxide, the remainder being hydrogen and methane, added as stream 8 to form acetic acid as described in Example 1. A stream 9 of 345 kg/h of water is added to reactor 104 in order to maintain a finite water concentration.

From reactor 104 is obtained a liquid stream 6 containing the acetic acid product corresponding to 18750 kg/h of acetic acid and a gaseous stream 7 containing methyl iodide, hydrogen, carbon dioxide and unconverted carbon monoxide and inerts such as methane.

The gaseous stream 7 is passed through reflux condenser 105 to recover part of condensibles comprising methyl iodide and acetic acid, which are recycled to the reactor 104 and the resulting gaseous stream 10 is passed to absorber 106, in which essentially all methyl iodide is recovered by absorption in liquid acetic acid. From absorber 106, the gaseous stream 12 is passed to the aforementioned absorber 102 for recovery of residual amounts of acetic acid originating from the wash and remaining traces of methyl iodide.

In this Example, 92.5% of the total carbon monoxide contained in the feed gas streams 1 and 9 is converted into acetic acid.

Example 3

Figure 3:
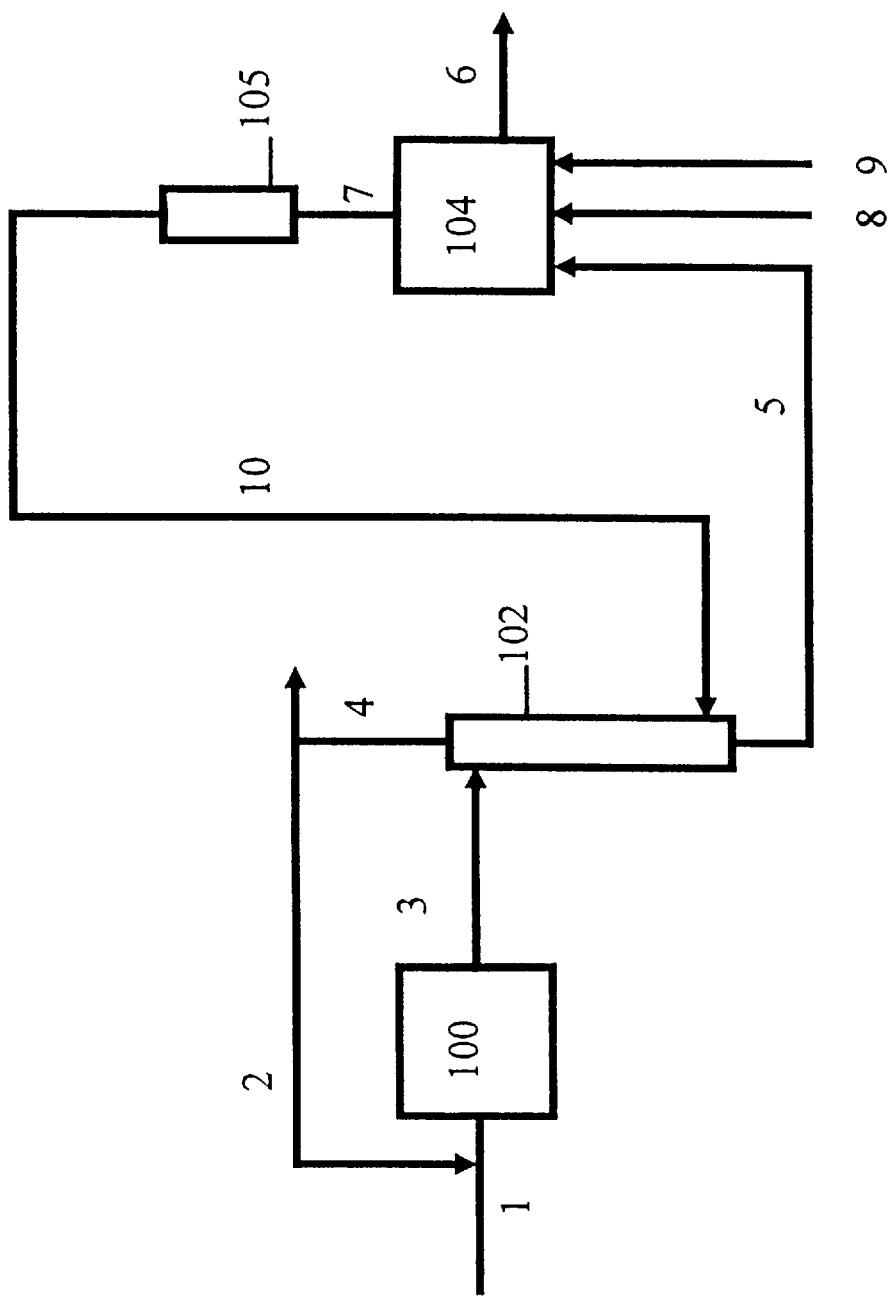
FIG. 3 shows an embodiment of the invention which is similar to the process for making acetic acid shown in FIG. 2, but in which the gas stream is passed directly to the absorber for recovery of methyl iodide and acetic acid.

In this Example, acetic acid is produced in a process similar to that of Example 2 except that the gas stream 10 is passed directly to the absorber 102 for recovery of methyl iodide and acetic acid. Reference is made to FIG. 3 and Table 3.

In this Example, 92.5% of the total carbon monoxide contained in the feed gas streams 1 and 9 are converted into acetic acid.

TABLE 1

| Stream No. | 1 | 3 | 5 | 9 | 10 | 12 |
|---|---|---|---|---|---|---|
| Flow, Nm³/h | 30223 | 151992 |  | 8760 | 1615 | 1520 |
| Flow, kg/h |  |  | 9950 |  |  |  |
| H₂ | 73.0 | 75.3 | 0.1 | 3.0 | 21.6 | 22.7 |
| CO | 25.5 | 1.9 |  | 93.0 | 51.0 | 53.5 |
| CO₂ |  | 3.4 | 0.4 |  | 2.3 | 0.5 |
| CH₄ | 1.1 | 2.9 |  | 4.0 | 22.0 | 23.2 |
| CH₃OH |  | 2.0 | 28.7 |  |  |  |
| (CH₃)₂O |  | 12.8 | 37.2 |  |  |  |
| H₂O | 0.4 | 1.7 | 33.6 |  | 0.1 |  |
| CH₃COOH |  |  |  |  | 0.1 | 0.1 |
| CH₃I |  |  |  |  | 2.9 | 0.00–033 |

TABLE 2

| Stream | 1 | 3 | 5 | 9 | 10 | 12 |
|---|---|---|---|---|---|---|
| Flow, Nm³/h | 27523 | 144640 |  | 8760 | 1615 | 1520 |
| Flow, kg/h |  |  | 9960 |  |  |  |
| H₂ | 73.0 | 67.3 | 0.1 | 3.0 | 21.6 | 22.7 |
| CO | 25.5 | 2.7 |  | 93.0 | 51.0 | 53.5 |
| CO₂ |  | 5.4 | 0.7 |  | 2.3 | 0.5 |
| CH₄ | 1.1 | 7.2 |  | 4.0 | 22.0 | 23.2 |
| CH₃OH |  | 2.0 | 29.3 |  |  |  |
| (CH₃)₂O |  | 13.7 | 37.2 |  |  |  |
| H₂O | 0.4 | 1.7 | 32.6 |  | 0.1 |  |
| CH₃COOH |  |  | 0.03 |  | 0.1 | 0.1 |
| CH₃I |  |  | 0.00007 |  | 2.9 | 0.00033 |

TABLE 3

| Stream No. | 1 | 3 | 5 | 9 | 10 |
|---|---|---|---|---|---|
| Flow, Nm³/h | 27523 | 144640 |  | 8760 | 1615 |
| Flow, kg/h |  |  | 10250 |  |  |
| H₂ | 73.0 | 67.3 | 0.1 | 3.0 | 21.7 |
| CO | 25.5 | 2.7 |  | 93.0 | 51.0 |
| CO₂ |  | 5.4 | 0.7 |  | 2.3 |
| CH₄ | 1.1 | 7.2 |  | 4.0 | 21.9 |
| CH₃OH |  | 2.0 | 29.2 |  |  |
| (CH₃)₂O |  | 13.7 | 37.0 |  |  |
| H₂O | 0.4 | 1.7 | 32.3 |  | 0.1 |
| CH₃COOH |  |  | 0.02 |  | 0.1 |
| CH₃I |  |  | 0.7 |  | 2.9 |

I claim:

1. A process for the preparation of acetic acid product comprising, in a first catalytic step, conversion of a hydrogen and carbon monoxide containing synthesis gas to obtain a liquid process stream comprising methanol and, in a second catalytic step, carbonylation of the process stream with carbon monoxide to a product stream being rich in the acetic acid product in presence of catalytic effective amounts of a metal compound selected from Group VIII of the Periodic Table promoted with a halide compound, the improvement comprising the further steps of:
   (i) withdrawing from the carbonylation step a vent gas stream comprising carbon monoxide and residual amounts of acetic acid and halide compound;
   (ii) separating the vent gas stream into a liquid fraction containing a part of the residual amounts of acetic acid and part of the halide compound and a gaseous fraction with the carbon monoxide and remaining amounts of acetic acid and halide compound;
   (iii) recycling the liquid fraction to the carbonylation step;
   (iv) subjecting the gaseous fraction to liquid absorption to remove the acetic acid and halide compound in the gaseous fraction to obtain a carbon monoxide rich recycle stream; and
   (v) introducing the carbon monoxide rich recycle stream into the synthesis gas conversion step.

2. The process of claim 1, wherein the hydrogen and carbon monoxide containing synthesis gas are converted, in the first catalytic step, into a process stream containing methanol and dimethyl ether.

3. The process of claim 1, wherein the residual amounts of acetic acid and halide compound in step (iv) are recovered by liquid absorption in acetic acid, and, subsequently, in the liquid process stream.

4. The process of claim 1, wherein the residual amounts of acetic acid and halide compound in step (iv) are recovered by liquid absorption in the liquid process stream.

5. The process of claim 2, wherein the residual amounts of acetic acid and halide compound in step (iv) are recovered by liquid absorption in acetic acid, and, subsequently, in the liquid process stream.

6. The process of claim 2, wherein the residual amounts of acetic acid and halide compound in step (iv) are recovered by liquid absorption in the liquid process stream.

* * * * *